United States Patent
Alvarez Hernandez

(10) Patent No.: US 6,432,388 B1
(45) Date of Patent: Aug. 13, 2002

(54) WHITENING ANTI-PLAQUE AND ANTI-TARTAR LOW ABRASIVITY TOOTH PASTE

(75) Inventor: Maria Alvarez Hernandez, Madrid (ES)

(73) Assignee: Biocosmetics, S.L., Madrid (ES)

(*) Notice: Subject to any disclaimer, the term of this patent is extended or adjusted under 35 U.S.C. 154(b) by 0 days.

(21) Appl. No.: 09/554,159

(22) PCT Filed: Nov. 13, 1998

(86) PCT No.: PCT/ES98/00310

§ 371 (c)(1),
(2), (4) Date: May 9, 2000

(87) PCT Pub. No.: WO99/25315

PCT Pub. Date: May 27, 1999

(30) Foreign Application Priority Data

Nov. 14, 1997 (SE) .............................. 9702390

(51) Int. Cl.[7] .............................. A61K 7/16; A61K 7/20; A61K 7/28; A61K 7/18
(52) U.S. Cl. .............................. 424/50; 424/49; 424/52; 424/57
(58) Field of Search ..................... 424/49–88

(56) References Cited

U.S. PATENT DOCUMENTS

| | | | | |
|---|---|---|---|---|
| 4,986,981 A | * | 1/1991 | Glace et al. ............. | 424/50 |
| 5,320,830 A | * | 6/1994 | Lvkacovic et al. ...... | 424/52 |
| 5,320,831 A | * | 6/1994 | Majeti et al. ............ | 424/49 |
| 5,431,903 A | * | 7/1995 | Majeti et al. ............ | 424/50 |
| 5,437,856 A | * | 8/1995 | Lvkacovic et al. ...... | 424/50 |
| 6,228,402 B1 | * | 5/2001 | Wolf et al. .............. | 426/94 |
| 6,241,973 B1 | * | 6/2001 | Rinnb ...................... | 424/50 |

FOREIGN PATENT DOCUMENTS

| | | | |
|---|---|---|---|
| DE | 1948468 | * | 4/1971 |
| ES | 2079325 | * | 1/1996 |
| ES | 2095812 | * | 2/1997 |
| FR | 2 600 535 | * | 12/1987 |
| GB | 13 75450 | * | 11/1974 |
| GB | 1514469 | * | 6/1978 |
| GB | 22 89 841 | * | 12/1995 |
| GB | 2 289 841 | * | 12/1995 |
| GB | 2 290233 | * | 12/1995 |
| WO | 95/17 158 | * | 6/1995 |
| WO | 2001045660 | * | 6/2001 |

OTHER PUBLICATIONS

Rembrandt (R) Whitening Toothpastes (Den–Mat) Labezgd Ingredients "Whitening Agents for Teeth" School Project Independent Study by Nicole B & Ivan Mack, Dec. 18, 2000.*

Rembrandt Website http://www.rembrandt.com/products (Copyright 1998–1999) Dec. 18, 2000.*

* cited by examiner

*Primary Examiner*—Shep K. Rose
(74) *Attorney, Agent, or Firm*—Ladas & Parry

(57) ABSTRACT

The improvements consist of formulation of a whitening toothpaste, which is anti-plaque and anti-tartar, of low abrasion, which is suitable for treating sensitive teeth and which lacks detergents, that comprises 0.1–1% papain, 5–10% xylitol, 16–18% of an abrasive system based on silica, a buffer consisting of tetra-potassium pyrophosphate and potassium dihydrogen phosphate [pH 7 approximately], along with water, binding agents, aromatizing agents, colouring agents, preservatives, sweeteners, humectants, lubricants, opacifiers, re-mineralizing agents and vitamins A, B5, C, E or mixtures thereof.

15 Claims, No Drawings

WHITENING ANTI-PLAQUE AND ANTI-TARTAR LOW ABRASIVITY TOOTH PASTE

FIELD OF THE INVENTION

This invention relates to some improvements made to the object of the Spanish patent application no. P9401832 relating to a whitening toothpaste which is anti-plaque and anti-tartar of low abrasion, optionally suitable for the treatment of sensitive teeth, consisting of the formulation of a whitening toothpaste which is anti-plaque and anti-tartar of low abrasion, which, contrary to the toothpaste described in said Spanish patent application, has a greater proteolytic enzyme content and lacks detergents.

BACKGROUND OF THE INVENTION

The Spanish patent application no. P9401832 describes a whitening toothpaste which is anti-plaque and anti-tartar of low abrasion, optionally suitable for the treatment of sensitive teeth, that comprises 5–10% of xylitol, 0.7–1.1% of sodium laurysarcosinate, 16–18% of silica, 3–7% of a proteolytic enzyme with low specificity, or alternatively, 0.3–3% carbamide peroxide, along with a buffer, water, humectants, re-mineralising agents, bining agents, opacifiers, colouring agents, aromatising agents, sweeteners and preservatives.

In the whitening toothpaste formulation, which is anti-plaque and anti-tartar, of low abrasion, the buffer used consists of a mixture of tetra-sodium pyrosulphate and di-sodium dihydrogenopyrophosphate, while in the whitening toothpaste formulation, which is anti-plaque and anti-tartar of low abrasion and desensitising, that is to say, suitable for the treatment of sensitive teeth, the buffer used consists of a mixture of tetra-potassium pyrophosphate and di-potassium dihydrogenopyrophosphate.

The production of the whitening toothpaste, which is anti-plaque and anti-tartar, of low abrasion, encounters problems with the solubility of the sodium salts that make up the working buffer.

The Spanish addition certificate application no. P9501732 solves the aforementioned problem by using a potassium buffer, consisting of a mixture of potassium salts, along with a reduction in the xylithol content and the use of a humectation system that comprises a mixture of glycerine and sorbitol, and provides a the whitening toothpaste, which is anti-plaque and anti-tartar of low abrasion and which is suitable for the treatment of sensitive teeth, that comprises 1–5% xylitol, 1.5–2% sodium laurylsarcosinate, 16–18% silica, a buffer consisting of 4–5% tetra-potassium pyrosulphate and 1–3% of potassium dihydrogenopyrophosphate, 3–7% of a proteolytic enzyme with low specificity, or alternatively, 0.3–3% of carbamide peroxide.

An occurrence in common between the toothpastes described in the Spanish patent application P9401832 and in the Spanish addition certificate application no. P9501732 is the presence of a detergent, such as sodium laurylsarcosinate in a quantity lying between 1.5 and 2% by weight. The usual toothpastes also include a detergent in their formulation, generally sodium laurylsulphate (SLS).

However, the use of such detergents can seriously damage gums and lead to a series of alterations to the mucous, such as desquamtation of the oral mucus, irritation and foreshortening (B. B. Herlosfoson and P. Barkvoll, *Acta Odontol. Scand.*, 1993, 51: 39–43, "Desquamative effect of sodium lauryl sulfate on oral mucosa. A preliminary study"; B. B. Herlosfoson and P. Barkvoll, *Eur. J Oral Sci.*, 1996, 104, 21–26, "Oral mucosal desquamation caused by two toothpaste detergents in an experimental model"; B. B. Herlosfoson and P. Barkvoll, *J Clin. Periodontol.*, 1996, 24, 1–5, "Oral mucosal desquamation of pre- and post- menopausal women"). Similarly, SLS significantly increases the appearances of new ulcers in patients with recurrent ulcers or cankers (B. B. Herlosfoson and P. Barkvoll, *Acta Odontol. Scand.*, 1994, 52:257–259, "Sodium lauryl sulfate and recurrent aphthous ulcers. A preliminary study"; B. B. Herlosfoson and P. Barkvoll, *Acta Odontol. Scand.*, 1996, 54:150–153, "The effect of two toothpaste detergents on the frequency of recurrent aphthous ulcers") and provokes rapid vasodilation with an increased blood flow when applied to the lips (B. B. Herlofson, P. Brodin and H Aars, *J Clin. Periodontol.*, 1996, 23(11), "Increased human gingival blood flow induced by sodium lauryl sulfate").

It seems that these adverse effects of SLS are due to the surfactant nature of SLS, to its affinity for glycoproteins and to his ability to fix calcium ions. SLS can even lead to the disintegration of the mucin layer, denaturing of the proteins of the epithelial cells and the dissolving of the structural lipids of the cells, provoking finally the penetration of SLS into the deepest layers of the mucus where the functioning of the live tissue can be compromised.

On the other hand, the toothpaste formulations described in the Spanish patent application P9401832 and in its addition certificate no P9501732 have a relatively high content of proteolytic enzyme with low specificity (papain), lying between 3 and 7% by weight, which could influence the cost of the product and lead to irritations of the mouth.

The invention provides a solution to the aforementioned problems which consists of some improvements introduced in the formulation of the toothpaste that comprise eliminating SLS and reducing the quantity of papain.

DETAILED DESCRIPTION OF THE INVENTION

The invention provides some improvements introduced into the object of the Spanish patent application P9401832 relating to a whitening toothpaste which is anti-plaque and anti-tartar of low abrasion, consisting of the development of a whitening toothpaste which is anti-plaque and anti-tartar of low abrasion and which is suitable for treating sensitive teeth, that is characterised by the lack of detergents and whose formulation comprises:

| Component | % by weight with respect to total |
| --- | --- |
| Papain | 0.1–1 |
| Xylitol | 5–10 |
| abrasive system based on silica | 16–18 |
| a buffer consisting of: | |
| i) tetra-potassium pyrophosphate | 4–5 |
| ii) potassium dihydrogen phosphate | 1–3 |
| additives/excipients | s.q. |

[s.q.: sufficient quantity to make up 100%]

Papain is a proteolytic enzyme with low specificity, suitable for cleaning the salivary protein plaque that has a whitening effect on the tooth surfaces. A valued enzymatic extract can be used, whose proteolytic activity has been adjusted to a constant value, from a latex obtained from unripe fruits of the *Carica papaya* (papaya). Papain hydrolysed proteins, amides and amino acid esters, and its activity is associated with the presence of free sulphyl (—SH)

groups in its active center. To produce the toothpaste of this invention, an enzymatic extract is preferably used that contains papain with a proteolytic activity of, approximately, 6,000 U-USP/mg [Units of United States Pharmacopea]. The optimum working temperature for this enzyme lies between 40 and 65° C. Due to the low substrate specificity, papain can act on multiple protein products, in over pH range of from 3 to 9. Outside these values the enzyme is inactive. In general, the toothpaste that contains papain conveniently has a pH near to neutral, that is to say, approximately 7, with a view to guaranteeing the activity of the enzyme without de-mineralising the enamel. Papain has a cleaning action on the bacterial plaque and tartar by breaking the glycoprotein and lipoprotein chains from the saliva fluid as well as acting on the bacterial excretory activity of mucylaginose substances (capsule) that attach themselves to the enamel allowing colonisation by bucal flora (bacterial plaque) and the fixing of calcium salts to these structures that act as supports (tartar). Therefore, by attacking these structures, the processes associated with plaque and tartar excess are improved such as tooth decay and periodontal disease.

The xylitol is active in several ways as, on the one hand, it acts as a humectant and refresher. while on the other, it has voluminous anti-tooth decay sweetening activity and inhibits capture and metabolism of glucose by certain bacteria, preventing the formation of organic acids, that attack the hydroxyapatite of the enamel dissolving it and provoking the appearance of tooth decay. Furthermore, the xylitol has the ability to reduce the adhesivity of the bacterial species *Stretococcus mutans,* a microbial agent directly related with the processes of tooth decay.

The abrasive system of the toothpaste provided by this invention consists of a mixture of viscous and abrasive precipitated silica (Handbook of Pharmaceutical Excipients, The Pharmaceutical Society of Great Britain, 1 Lambeth High Street, London SE 1 7JN, England, pages 253–256). The former is used for its thixotropic properties and the latter for its greater effectiveness when removing adherent substances from the dental surfaces. The use of these products guarantees a low abrasion as they are amorphous solids of average hardness. They are also fully compatible with fluoride, which is used as a re-mineralising agent, as they do not contain calcium salts that reduce its solubility which reduces its bioavailability.

As was mentioned earlier, the toothpaste provided by this invention is conveniently prepared with a buffer at a pH near to neutral (pH ≈7), with a view to guaranteeing the activity of the papain and protecting the enamel from an acidic pH. For these purposes a buffer consisting of tetra-potassium pyrophosphate and potassium dihydrogenophosphate at suitable concentrations can be used to maintain the pH at a value of approximately 7. The presence of potassium ions has a desensitising effect as will be discussed below.

The formulation of the toothpaste object of this invention also contains conventional additives and excipients suitable for improving its properties and characteristics, and for facilitating its processing. These may me selected from water, binding agents, aromatising agents, colouring agents, preservatives, sweeteners, humectants, lubricants, opacifiers, re-mineralising agents, vitamins and mixtures thereof.

As a binding agent any of those normally used in the manufacture of these types of formulation can be used, for example, tragacant gum. The binding agent can be present in the formulation at an amount lying between 0.5 and 1.5% by weight with respect to the total.

The toothpaste can be aromatised by means of the addition of a suitable conventional aromatising agent, for example, preferably an aroma of mint. The aromatising agent can be present in the formulation at an amount lying between 0.5 and 1.5 % by weight with respect to the total.

As a colouring agent any of those normally used in the formulation of toothpastes can be used, for example, FCF Brilliant blue, CI.42090 [KIRSCH PHARMA]. The colouring agent can be present in the formulation at an amount lying between 0.001 and 0.005% by weight with respect to the total.

The preservative can be any of the normal ones such as a derivative of benzoic acid, for example methyl p-hydroxybenzoate. The preservative can be present in the formulation at an amount lying between 0.1 and 0.3% by weight with respect to the total.

For example, as an sweetener, sodium sacharrine or cyclamic acid and derivatives thereof can be used, for example, sodium cyclamate. The sweetener can be present in the formulation in at an amount lying between 0.08 and 0.15% by weight with respect to the total.

The humectant agent used to prevent desiccation and hardening of the toothpaste is a mixture of sorbitol and glycerine, along with the aforementioned xylitol. Sorbitol may be present in the formulation at an amount lying between 35 and 45% by weight with respect to the total, while the glycerine may be present in the formulation at an amount lying between 5 and 10% by weight with respect to the total.

The lubricant can be any of those normally used in toothpaste formulations, for example, dimethycone (polymer of dimethylpolysiloxane), which is a surfactant that contributes to conferring good theological properties on the toothpaste object of this invention. The lubricant may be found in the formulation at an amount lying between 0.25 and 0.75% by weight with respect to the total.

As an opacifier any of the normal opacifiers may be used, for example, titanium dioxide. The opacifier may be present in the formulation at an amount lying between 0.05 and 1% by weight with respect to the total.

As a re-mineralising agent a fluoride source is used, such as sodium fluoride, as in this way 100% active flouride is obtained as a re-mineralising agent for the white lesions produced by organic acids arising from bacterial fermentation. The re-mineralising agent can be present in the formulation at an amount lying between 0.2 and 0.4% by weight with respect to the total.

The toothpaste provided by this invention can also contain, if so desired, a vitamin selected from the group formed by vitamin A, vitamin B5, vitamin C, vitamin E, and mixtures thereof. If they are used each vitamin can be present in the formulation at a quantity lying between 0.1 and 5% by weight with respect to the total. These vitamins can be used as they are, in the form of pro-vitamins or in the form of pharmaceutically acceptable salts. Vitamin A, which is usually used in the form of palmitate salt, promotes the epithelialisation of oral mucus and protects the gums. Vitamin B5, more specifically D-pantenol, has a soothing, curative, anti-inflammatory effect on epithelial lesions, promotes the epithelialisation of injuries and softens scar tissue, and is suitable for the treatment of injuries produced as a consequence of dental extractions, gingivitis, stomatitis, pain produced by putting false teeth in place, ulcers, traumatic lesions of the mucus and chronic and recurrent cankers. Vitamin C regenerates the epithelium of the oral mucus, stimulates the synthesis of collagen and the immune system (inflammation mechanism) and increases the capacity for protection of the phagocyte cells against bacteria. Vitamin E, which is usually used in the form of acetate salt, has a calming and anti-inflammatory effect, protects oral mucus against lipid peroxidation due to the formation of free radicals and against environmental contaminants (ozone, cigarette smoke, etc.) and favours the healing of injuries. By the incorporation of all or some of the aforementioned vitamins, the invention provides toothpastes that, as well as the aforementioned characteristics, have anti-inflammatory properties and are effective soothing agents, and that increase the protective properties of the membranes of the oral mucus, reduce the occurrence of plaque and gingival as well as bacterial contamination.

In a particular embodiment of this invention, a toothpaste is provided whitening toothpaste which is anti-plaque and anti-tartar of low abrasion, suitable for the treatment of sensitive teeth, of the formula:

| Components | % by weight with respect to total |
|---|---|
| Papain | 0.1–1 |
| Xylitol | 5–10 |
| Abrasive systern based on silica | 16–18 |
| Buffer consisting of: | |
| i) tetra-potassium pyrophosphate | 4–5 |
| ii) potassium dihydrogen phosphate | 1–3 |
| Binding agent | 0.5–1.5 |
| Aromatising agent | 0.5–1.5 |
| Colouring agent | 0.001–0.005 |
| Preservative | 0.1–0.3 |
| Sweetener | 0.08–0.15 |
| Sorbitol | 35–45 |
| Glycerine | 5–10 |
| Lubricant | 0.25–0.75 |
| Opacifier | 0.05–1 |
| Re-mineralising agent | 0.2–0.4 |
| Vitamin (*) | 0.1–20 |
| Water | 10–25 |

(*) The vitamin is selected from the group formed by vitamins A, B5, C, E and mixtures thereof. The composition can have one or several vitamins in a proportion lying between 0.1 and 5% by weight of each one of the vitamins.

The desensitising activity of the toothpaste of this invention follows a strategy that consists of blocking the electrochemical mechanism that allows neuronal stimulation. As is know, for a neurone to be stimulated or transmit a nervous impulse it needs to be polarised, that is to say, there has to be a difference in electrical potential between the inner face of the cellular membrane and the external one. This difference in electrical potential is due to an unequal distribution of two cations on each side of the membrane. These cations are mainly sodium and potassium ions. An active transporter exists in the neuronal membrane that introduced potassium into the cell and removes sodium to the exterior, against the concentration gradient, in a ration 3:2, so that a potential gradient is formed. By introducing a potassium salt into the toothpaste, such as the working buffer, in a high concentration, the nerve ends are temporally depolarised which inhibits their capacity for stimulation and transmission.

As can be appreciated, different active ingredients are combined in the toothpaste provided by this invention which attack the processes of formation of dental plaque and tartar (mineralised dental plaque) by different mechanisms. These structures are the origin of different pathological processes (tooth decay and periodontal disease) and the combination of such active ingredients produces a synergistic effect. These products are listed below:

xylitol, which reduces the ability of the bacteria to adhere to the enamel by affecting the bacterial metabolism and the capacity to form capsules in plaque bacteria;

the buffer used consisting of tetra-potassium pyrophosphate and potassium dihydrogen phosphate, which ensures a desensitising effect without losing the advantages of minimal abrasion or the anti-plaque or anti-tartar effect, which constitutes one of the objectives of the toothpaste of this invention; and papain as a proteolytic enzyme which assures a non-abrasive cleaning effect which constitutes another of the objectives of the toothpaste of this invention.

Therefore, the improvements provided by this invention give rise to a whitening toothpaste which is anti-plaque and anti-tartar, of low abrasion, and desensitising, able to eliminate stains from tooth surfaces without damaging them and maintaining these surfaces free of plaque and dental deposit, achieving a whitening effect for the tooth surface, all this with a minimal abrasion. If the user suffers from sensitive teeth, the toothpaste blocks the capacity of the nerve ends originating from the trigenimy found in the dentin to give an algic response.

The toothpaste provided by this invention can be easily prepared by mixing the different components in suitable quantities in a reactor equipped with a form of stirring, and a temperature that does not lead to degradation or thermal denaturing of the enzyme, that is to say, at temperatures lower than 65° C.

The following example is illustrative of this invention and should not be considered to limit the scope of the present invention.

EXAMPLE 1

Preparation of a Toothpaste

A toothpaste was prepared with the following formulation:

| Components | % by weight with respect to total |
|---|---|
| Papain | 0.9 |
| Xylitol | 9 |
| Abrasive system based on silica | 17 |
| Buffer consisting of: | |
| i) tetra-potassium pyrophosphate | 4.6 |
| ii) potassium dihydrogen phosphate | 1.8 |
| Tragacant gum | 0.5 |
| Mint aroma | 0.9 |
| CI 42090 (KIRSCH PHARMA) colorant | 0.003 |
| Methyl p-hydroxybenzoate | 0.26 |
| Sweetener | 0.12 |
| Sorbitol | 38.207 |
| Glycerine | 7 |
| Dimethicone 100 cSk | 0.5 |
| Titanium dioxide | 0.09 |
| Sodium fluoride | 0.32 |
| Water | 18.8 |

For the production of a toothpaste a reactor was loaded with a suitable quantity of glycerine and sorbitol, in the form of a 70% solution. The binding agent was then dispersed (tragacant gum) using a turbo-stirrer with a view to avoiding the formation of aggregations. Once the mixture was fully homogeneous (without aggregations), the indicated quantity of purified water was added and stirring continued. Then, with rapid stirring, the colouring, preservative (methyl p-hydroxybenzoate), titanium dioxide, sodium fluoride, xylitol, tetra-potassium pyrophosphate and potassium di-hydrogen phosphate were added successively. The rapid stirrer was stopped, and the slow stirrer connected and the indicated amount of papain (6,000 U-USP of activity) was added until perfected dissolved. Then, the abrasive precipitated silica was added, and the container evacuated in order to remove the air from the toothpaste. The thickening silica was added in five aliquoted fractions. Finally, the aromatising agent (mint aroma) and the dimethicone (kinetic viscosity 100 cSk) were added.

The toothpaste obtained had good rheological properties and proved to be stable. It had suitable abrasion and efficacy. This toothpaste can be used in cases of sensitive teeth.

EXAMPLE 2

Preparation of a Vitamin-supplemented Toothpaste

Following a procedure similar to that described in Example 1 a vitamin supplemented toothpaste was prepared with the following formulation.

| Components | % by weight with respect to total |
|---|---|
| Papain | 0.9 |
| Xylitol | 9 |
| Abrasive system based on silica | 17 |
| Buffer consisting of: | |
|     i) tetra-potassium pyrophosphate | 4.6 |
|     ii) potassium dihydrogen phosphate | 1.8 |
| Tragacant gum | 0.5 |
| Mint aroma | 0.9 |
| CI 42090 (KIRSCH PHARMA) colourant | 0.003 |
| Methyl p-hydroxybenzoate | 0.26 |
| Sweetener | 0.12 |
| Sorbitol | 36.207 |
| Glycerine | 6.5 |
| Dimethicone 100 cSk | 0.5 |
| Titanium dioxide | 0.09 |
| Sodium fluoride | 0.32 |
| Vitamin B5 (pantenol) | 1 |
| Vitamin E acetate | 1.5 |
| Water | 18.8 |

The toothpaste obtained also has calming and anti-inflammatory effects.

What is claimed is:

1. A whitening toothpaste which is anti-plaque and anti-tartar, of low abrasion, and suitable for treating sensitive teeth, and which comprises the following ingredients in weight percent:

Papain 0.1–1

Xylitol 5–10 an abrasive system based on silica 16–18 a buffer consisting of:
    i) tetra-potassium pyrophosphate 4–5
    ii) potassium dihydrogen phosphate 1–3 additives/excipients s.q. [s.q.: sufficient quantity to make up 100%]

said toothpaste being free of detergents.

2. A toothpaste according to claim 1, in which said additives/excipients are selected from the group formed by water, binding agents, aromatising agents, colouring agents, preservatives, sweeteners, humectants, lubricants, opacifiers, re-mineralising agents, vitamins and mixtures thereof.

3. A toothpaste according to claim 2, whose humectant system comprises a mixture of glycerine and sorbitol, consisting of 5–10% of glycerine, by weight, with respect to the total of the formulation and 35–45% of sorbitol, by weight, with respect to the total of the formulation.

4. A toothpaste according to claim 2, that comprises sodium fluoride as re-mineralising agent in a proportion lying between 0.2% and 0.4% by weight, with respect to the total of the formulation.

5. A toothpaste according to claim 2, that comprises a vitamin selected from the group formed by vitamin A, vitamin B5, vitamin C, vitamin E and mixtures thereof, in a proportion lying between 0.1% and 5% by weight of vitamin present with respect to the total weight of the formulation.

6. A whitening toothpaste, which is anti-plaque and anti-tartar, of low abrasion, and suitable for treating sensitive teeth, lacking detergents which comprises:

| Components | % by weight with respect to total |
|---|---|
| Papain | 0.1–1 |
| Xylitol | 5–10 |
| an abrasive system based on silica | 16–18 |
| a buffer consisting of: | |
|     i) tetra-potassium pyrophosphate | 4–5 |
|     ii) potassium dihydrogen phosphate | 1–3 |
| Binding agent | 0.5–1.5 |
| Aromatising agent | 0.5–1.5 |
| Colouring agent | 0.001–0.005 |
| Preservative | 0.1–0.3 |
| Sweetener | 0.08–0.15 |
| Sorbitol | 35–45 |
| Glycerine | 5–10 |
| Lubricant | 0.25–0.75 |
| Opacifier | 0.05–1 |
| Re-mineralising agent | 0.2–0.4 |
| Water | 10–25 |

7. A toothpaste according to claim 6, that comprises:

| Components | % by weight with respect to total |
|---|---|
| Papain | 0.9 |
| Xylitol | 9 |
| Abrasive system based on silica | 17 |
| Buffer consisting of: | |
|     i) tetra-potassium pyrophospbate | 4.6 |
|     ii) potassium dihydrogen phosphate | 1.8 |
| Tragacant gum | 0.5 |
| Mint aroma | 0.9 |
| CI 42090 (KIRSCH PHARMA) colorant | 0.003 |
| Methyl p-hydroxybenzoate | 0.26 |
| Sweetener | 0.12 |
| Sorbitol | 38.207 |
| Glycerine | 7 |
| Dimethicone 100 cSk | 0.5 |
| Titanium dioxide | 0.09 |
| Sodium fluoride | 0.32 |
| Water | 18.8 |

8. A toothpaste according to claim 6, that also comprises a vitamin selected from the group formed by vitamin A, vitamin B5, vitamin C, vitamin E and mixtures thereof, in a proportion lying between 0.1% and 5% by weight of vitamin present with respect to the total of the formulation.

9. A toothpaste according to claim 8, that comprises:

| Components | % by weight with respect to total |
|---|---|
| Papain | 0.9 |
| Xylitol | 9 |
| Abrasive system based on silica | 17 |
| Buffer consisting of: | |
| i) tetra-potassium pyrophosphate | 4.6 |
| ii) potassium dihydrogen phosphate | 1.8 |
| Tragacant gum | 0.5 |
| Mint aroma | 0.9 |
| CI 42090 (KIRSCH PHARMA) colorant | 0.003 |
| Methyl p-hydroxybenzoate | 0.26 |
| Sweetener | 0.12 |
| Sorbitol | 36.207 |
| Glycerine | 6.5 |
| Dimethicone 100 cSk | 0.5 |
| Titanium dioxide | 0.09 |
| Sodium fluoride | 0.32 |
| Vitamin B5 (pantenol) | 1 |
| Vitamin E acetate | 1.5 |
| Water | 18.8 |

10. The whitening toothpaste according to claim 1, wherein the toothpaste consists essentially of said ingredients.

11. A toothpaste consisting essentially of:
   a) a plurality of active ingredients which collectively inhibit the formation of dental plaque and tartar and promote whitening of the teeth of a user, said active ingredients consisting of
      i) xylitol in the amount of 5–10% by weight,
      ii) a buffer consisting of tetra-potassium pyrophosphate in an amount of 4–5% by weight, and
      iii) potassium dihydrogen phosphate in an amount of 1–3% by weight,
   b) an abrasive comprising silica; and
   c) a plurality of additives that make up the balance of the toothpaste.

12. A toothpaste according to claim 11, wherein said additives are selected from the group consisting of water, binding agents, aromatizing agents, coloring agents, preservatives, sweeteners, humectants, lubricants, opacifiers, re-mineralizing agents, vitamins and mixtures thereof.

13. A toothpaste according to claim 12, wherein said additives form a humectant system comprising a mixture of glycerine and sorbitol, said glycerine being present in the toothpaste in an amount of 5–10% by weight and said sorbitol being present in the toothpaste in an amount of 35–45% by weight.

14. A toothpaste according to claim 13 comprising sodium fluoride as a re- mineralizing agent in an amount of between 0.2% and 0.4% by weight.

15. A toothpaste according to claim 14, comprising a vitamin selected from the group consisting of vitamin A, vitamin B5, vitamin C, vitamin E and mixtures thereof, said vitamin being present in the toothpaste in an amount of between 0.1% and 5% by weight.

* * * * *